United States Patent [19]

Matsuishi et al.

[11] Patent Number: 4,816,459
[45] Date of Patent: Mar. 28, 1989

[54] TETRAZOLYL-SUBSTITUTED PYRIDO[1,2-A]PYRIMIDINES AND USE AS SRS-A ANTAGONISTS

[75] Inventors: Naoto Matsuishi, Kawaguchi; Yoshio Nakagawa, Kasukabe; Michiaki Amano, Koganei; Norihiko Kakehi, Yokohama; Toshio Kawashima, Saitama; Shigeki Omura, Tokyo, all of Japan

[73] Assignee: Tokyo Tanabe Co. Ltd., Japan

[21] Appl. No.: 913,869

[22] Filed: Oct. 1, 1986

[30] Foreign Application Priority Data

Oct. 3, 1985 [JP] Japan .................. 60-219126

[51] Int. Cl.$^4$ .................. C07D 471/04; A61K 31/505
[52] U.S. Cl. ........................ 514/258; 544/282
[58] Field of Search ............ 544/282, ; 514/258

[56] References Cited

U.S. PATENT DOCUMENTS

| | | | |
|---|---|---|---|
| 4,122,274 | 10/1978 | Juby | 544/249 |
| 4,192,944 | 3/1980 | Juby | 544/282 |
| 4,209,620 | 6/1980 | Juby | 514/826 |
| 4,474,953 | 10/1984 | Wade | 544/282 |
| 4,617,407 | 10/1986 | Young et al. | 548/254 |
| 4,667,055 | 5/1987 | Gillard et al. | 514/861 |

OTHER PUBLICATIONS

Finnegan et al., J. Amer. Chem. Soc., vol. 80, 3908–3911 (1958).

*Primary Examiner*—Donald G. Daus
*Assistant Examiner*—E. Bernhardt
*Attorney, Agent, or Firm*—McGlew and Tuttle

[57] ABSTRACT

Pyrido[1,2-a]pyrimidine derivatives of the general formula [I] and their physiologically acceptable salts are provided:

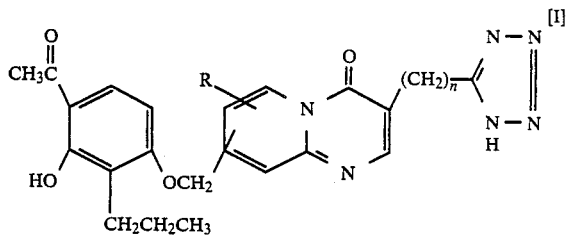

where R is a hydrogen atom, a halogen atom or a methyl group, and n is a whole number of 0, 1 or 2. The pyrido[1,2-a]-pyrimidine derivatives and their salts exhibit an excellent antagonistic effect on slow-reacting substance of anaphylaxis and, therefore, are useable for the treatment of allergic diseases.

32 Claims, No Drawings

TETRAZOLYL-SUBSTITUTED PYRIDO[1,2-A]PYRIMIDINES AND USE AS SRS-A ANTAGONISTS

BACKGROUND OF THE INVENTION (1) Field of the Invention

This invention relates to pyrido[1,2-a]pyrimidine derivatives and physiologically acceptable salts thereof, a process for preparing such compounds, and pharmaceutical compositions containing such a compound as an active ingredient. The pyrido[1,2-a]pyrimidine derivatives and physiologically acceptable salts thereof in accordance with the present invention have a marked antagonistic effect on slow-reacting substance of anaphylaxis (hereinafter abbreviated as SRS-A) and, therefore, can be used as drugs for the treatment of Type I allergic diseases induced by SRS-A.

(2) Description of the Prior Art

SRS-A is strongly effective in causing contraction of smooth muscle and constitutes a substance responsible for Type I allergic diseases, particularly bronchial asthma and allergic rhinitis [Quarterly Journal of Experimental Physiology, Vol. 30, p. 121, 1940]. Leukotriene $D_4$ has been found to be a representative active component of this substance and the presence of an inhibitory effect on the in vivo activity of leukotriene $D_4$ is now considered to be a criterion of the usefulness of a drug for the treatment of Type I allergic diseases induced by SRS-A [Nature, Vol. 288, p. 484, 1980].

Drugs useful for the treatment of Type I allergic diseases induced by SRS-A are roughly divided into two types: drugs of the SRS-A release suppression type which act to prevent the release of SRS-A from mast cells or basophils and thereby inhibit its activity indirectly, and drugs of the SRS-A antagonistic type which act to antagonize the released SRS-A in the living body and thereby inhibit its activity directly. However, drugs of the SRS-A release suppression type are inherently used for the purpose of preventing the induction of allergic attacks by SRS-A and generally tend to lack in effectiveness immediately after the onset of an attack. That is, they often fail to exhibit the so-called rapid-acting property. In recent years, therefore, it has been eagerly desired from the viewpoint of an immediate effect on allergic attacks to develop a satisfactorily effective drug of the SRS-A antagonistic type.

9-Methyl-3-(1H-tetrazol-5-yl)-4H-pyrido[1,2-a]pyrimidin-4-one potassium salt (hereinafter abbreviated as Compound TBX) is a conventionally known pyridopyrimidine compound and it has been reported that this compound is useful for the prevention of Type I allergic reactions (Japanese Patent Laid-Open No. 36294/'79).

SUMMARY OF THE INVENTION

However, a subsequent study has revealed that Compound TBX belongs to the SRS-A release suppression type (Japanese Journal of Allergology, Vol.33, No.9, p.728,1984). Moreover, a confirmatory experiment conducted by the present inventors has demonstrated that Compound TBX has no antagonistic effect on SRS-A as represented by leukotriene $D_4$. Accordingly, the present inventors have made an exhaustive study in the search for compounds antagonizing the in vivo activity of SRS-A and, in particular, leukotriene $D_4$. As a result, a novel compound having a marked antagonistic effect on leukotriene $D_4$ has surprisingly been discovered among compounds containing a pyrido[1,2-a]pyrimidine ring analogously to Compound TBX. The present invention has been completed on the basis of this discovery.

According to one feature of the present invention, there is provided a pyrido[1,2-a]pyrimidine derivative of the general formula [I]:

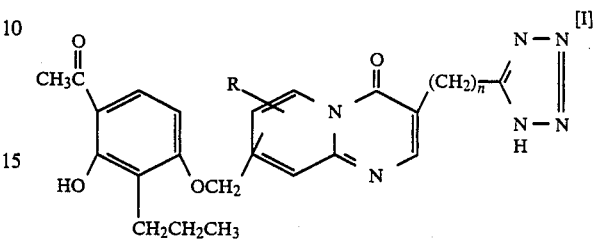

where R is a hydrogen atom, a halogen atom or a methyl group, and n is a whole number of 0, 1 or 2, or a physiologically acceptable salt thereof.

According to another feature of the present invention, there is provided a process for preparing pyrido[1,2-a]pyrimidine derivatives of the above general formula [I] and physiologically acceptable salts thereof.

According to still another feature of the present invention, there is provided a pharmaceutical composition useful for the treatment of allergic diseases containing, as an active ingredient, a pyrido[1,2-a]pyrimidine derivative of the above general formula [I] or a physiologically acceptable salt thereof.

DETAILED DESCRIPTION OF THE PREFERRED EMBODIMENTS

The pyrido[1,2-a]pyrimidine derivatives represented by the above general formula [I] (hereinafter referred to briefly as the present compounds [I]) can be prepared by reacting a nitrile compound of the general formula [II]:

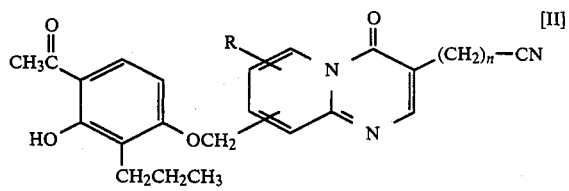

where R and n are as previously defined, with hydrazoic acid or a salt thereof.

Useful salts of hydrazoic acid include alkali metal salts such as sodium azide, potassium azide, etc.; alkaline-earth metal salts such as calcium azide, magnesium azide, etc.; salts formed by reaction with other metals, such as aluminum azide, tin azide, titanium azide, etc.; and salts formed by reaction with organic bases, such as ammonium azide, aniline azide, etc. Although such salts of hydrazoic acid may be used alone, alkali metal salts of hydrazoic acid should preferably be converted to aluminum azide, tin azide, ammonium azide, aniline azide or the like in the reaction system by using them in combination with a Lewis acid (such as aluminum chloride, tin chloride or the like) or a suitable salt (such as ammonium chloride, aniline hydrochloride or the like). The most preferable combination comprises sodium azide and aluminum chloride or ammonium chloride.

Suitable reaction solvents include ethers such as tetrahydrofuran, dioxane, etc.; and polar solvents such as dimethylformamide, dimethyl sulfoxide, dimethylacetamide, hexamethylphosphorotriamide, etc. The reaction is carried out by heating the reaction mixture at a temperature of 50° to 150° C. for a period of time ranging from 1 minute to 72 hours.

The present compound [I] prepared as above may be purified by recrystallization, by silica gel column chromatography, by converting the present compound [I] to a suitable salt and then neutralizing this salt to effect crystallization (hereinafter referred to as the crystallization procedure), or by a combination of these procedures.

Recrystallization solvents suitable for use in purification by recrystallization include water, methanol, ethanol, n-propyl alcohol, isopropyl alcohol, dimethylformamide, dimethyl sulfoxide, hexamethylphosphorotriamide, acetic acid, acetonitrile, trifluoroacetic acid and tetrahydrofuran, as well as mixtures of two or more such solvents. Developing solvents suitable for use in purification by silica gel chromatography include various mixtures of a halogenated hydrocarbon (such as chloroform, dichloromethane or the like) and an alcohol (such as methanol, ethanol or the like). Salts suitable for use in the crystallization procedure include sodium salts, potassium salts, calcium salts, magnesium salts and ammonium salts, and suitable neutralizing agents include mineral acids such as hydrochloric acid, sulfuric acid, nitric acid, etc., and organic acids such as acetic acid, formic acid, etc. Reaction solvents suitable for use in this crystallization procedure include water and various mixtures of water and an alcohol such as methanol, ethanol, isopropyl alcohol, n-butyl alcohol or the like.

Physiologically acceptable salts of the present compounds [I] can be prepared by reacting the corresponding compound [I] with an alkali metal or alkaline-earth metal hydroxide (such as sodium hydroxide, potassium hydroxide, calcium hydroxide, magnesium hydroxide or the like), an alkali metal or alkalineearth metal carbonate (such as sodium carbonate, potassium carbonate, calcium carbonate, magnesim carbonate or the like), an alcoholate of an alkali metal or an alkaline-earth metal (such as sodium, potassium, magnesium or the like), an organic amine (such as ethanolamine, methylephedrine or the like) or ammonia in water, an alcohol or a mixture thereof. Alcohols suitable for this purpose include methanol, ethanol, isopropyl alcohol, n-butyl alcohol and the like. The hydroxide, carbonate, alcoholate, organic amine or ammonia should be used in an amount of 0.5 to 6 moles, preferably 0.5 to 2 moles, per mole of the present compound [I].

The salt prepared as above may be purified by recrystallization, if necessary. Recrystallization solvents suitable for this purpose include water, methanol, ethanol, n-propyl alcohol, isopropyl alcohol, dimethylformamide, dimethyl sulfoxide, hexamethylphosphorotriamide, acetonitrile and tetrahydrofuran, as well as mixtures of two or more such solvents.

The present compound [I] or physiologically acceptable salt thereof prepared in the above-described manner may be dried according to any of conventional methods including warming, through-flow drying, freeze-drying and the like.

The nitrile derivatives represented by the above general formula [II] can be prepared by condensing 1 mole of a compound of the general formula [III]:

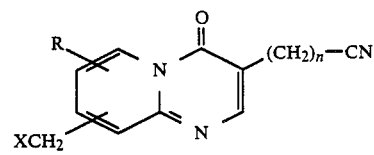

where R and n are as previously defined and X is a chlorine or bromine atom, with 1 to 6 moles of 2,4-dihydroxy-3-npropylacetophenone in the presence of an acid acceptor.

Acid acceptors useful for this purpose include alkali metal carbonates such as sodium carbonate, potassium carbonate, etc., and alkali metal hydroxides such as sodium hydroxide, potassium hydroxide, etc. In the reaction system, potassium iodide may also be present as a reaction accelerator.

Suitable reaction solvents include methanol, ethanol, isopropyl alcohol, n-butyl alcohol, acetone, methyl ethyl ketone, diethyl ketone, cyclohexanone, dimethylformamide, dimethyl sulfoxide, mixtures of two or more such solvents, and mixtures of water and such solvents. The reaction is carried out by heating the reaction mixture at a temperature of 50° to 110° C. for a period of time ranging from 1 minute to 72 hours.

The compounds represented by the above general formula [III] can be prepared (1) by halogenating a compound of the general formula [IV]:

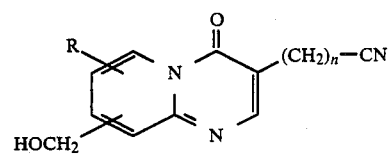

where R and n are as previously defined, with the aid of a halogenating agent such as thionyl chloride, phosphorus trichloride, phosphoryl chloride, phosphorus tribromide, phosphoryl bromide or the like, or (2) by halogenating and dehydrating a compound of the general formula [V]:

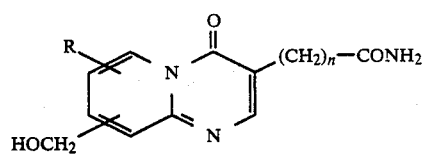

where R and n are as previously defined, with the aid of a halogenating agent such as phosphoryl bromide, phosphoryl chloride, thionyl chloride or the like. Compounds of the above general formula [III] in which n is equal to 0 can also be prepared by halogenating a compound of the general formula [VI]:

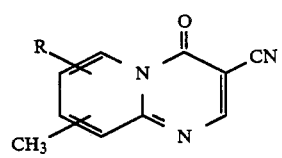

where R is as previously defined, with the aid of N-chlorosuccinimide or N-bromosuccinimide.

The antagonistic effect on SRS-A of the present compounds [I] and physiologically acceptable salts thereof was tested according to the following experimental procedures using leukotriene $D_4$ which is a representative active component of SRS-A. The test compounds used for this purpose were the compounds enumerated below and considered to be typical examples of the present compounds [I] and physiologically acceptable salts thereof. The designation given in parentheses after the chemical name of each compound means its tentative name as used herein and corresponds to the respective one of the examples which will be described later.

9-[(4-Acetyl-3-hydroxy-2-n-propylphenoxy)methyl]-3-(1H-tetrazol-5-yl)-4H-pyrido[1,2-a]pyrimidin-4-one (Example 1).

7-[(4-Acetyl-3-hydroxy-2-n-propylphenoxy)methyl]-3-(1H-tetrazol-5-yl)-4H-pyrido[1,2-a]pyrimidin-4-one (Example 2).

8-[(4-Acetyl-3-hydroxy-2-n-propylphenoxy)methyl]-3-(1H-tetrazol-5-yl)-4H-pyrido[1,2-a]pyrimidin-4-one (Example 3).

9-[(4-Acetyl-3-hydroxy-2-n-propylphenoxy)methyl]-7-bromo3-(1H-tetrazol-5-yl)-4H-pyrido[1,2-a]pyrimidin-4-one (Example 4).

9-[(4-Acetyl-3-hydroxy-2-n-propylphenoxy)methyl]-7-methyl-3-(1H-tetrazol-5-yl)-4H-pyrido[1,2-a]pyrimidin-4-one (Example 5).

9-[(4-Acetyl-3-hydroxy-2-n-propylphenoxy)methyl]-3[(1H-tetrazol-5-yl)methyl]-4H-pyrido[1,2-a]pyrimidin-4-one (Example 6).

7-[(4-Acetyl-3-hydroxy-2-n-propylphenoxy)methyl]-3[(1H-tetrazol-5-yl )methyl]-4H-pyrido[1,2-a]pyrimidin-4-one (Example 7).

9-[(4-Acetyl-3-hydroxy-2-n-propylphenoxy)methyl]-7methyl-3-[(1H-tetrazol-5-yl)methyl]-4H-pyrido[1,2-a]pyrimidin-4-one (Example 8).

9-[(4-Acetyl-3-hydroxy-2-n-propylphenoxy)methyl]-3[2-(1H-tetrazol-5-yl)ethyl]-4H-pyrido[1,2-a]pyrimidin-4-one (Example 9).

8-[(4-Acetyl-3-hydroxy-2-n-propylphenoxy)methyl ]-3[2-(1H-tetrazol-5-yl)ethyl]-4H-pyrido[1,2a]pyrimidin-4-one (Example 10).

9-[(4-Acetyl-3-hydroxy-2-n-propylphenoxy)methyl]-7-bromo-3-[2-(1H-tetrazol-5-yl)ethyl]-4H-pyrido[1,2-a]pyrimidin-4-one (Example 11).

9-[(4-Acetyl-3-hydroxy-2-n-propylphenoxy)methyl]-3-(1H-tetrazol-5-yl)-4H-pyrido[1,2-a]pyrimidin-4-one potassium salt (Example 12).

9-[(4-Acetyl-3-hydroxy-2-n-propylphenoxy)methyl]-3-[2-(1H-tetrazol-5-yl)ethyl]-4H-pyrido[1,2-a]pyrimidin-4-one potassium salt (Example 13).

(i) In vitro tests

The antagonistic effect on leukotriene $D_4$ of the present compounds [I] and physiologically acceptable salts thereof was tested by using the terminal ileum excised from a male guinea pig of the Hartley strain. Specifically, the terminal ileum was suspended, under aerated conditions, in 10 ml of Tyrode's solution containing $5 \times 10^{-7}$ M atropine and $1 \times 10^{-6}$ M mepyramine. Then, a test compound and leukotriene $D_4$ (manufactured by Wako Junyaku Co., Ltd.) were successively added thereto with an interval of 30 seconds. After the lapse of 4 to 6 minutes, the degree of contraction of the ileum was measured with a Model TD-112S Isotonic Transducer (manufactured by Nippon Koden Co., Ltd.). The test compound and leukotriene $D_4$ were used in such amounts as to give concentrations of $10^{-9}$ to $10^{-3}$ g/ml and 0.3 ng/ml, respectively.

The antagonistic effect on leukotriene $D_4$ of each test compound was evaluated in terms of the concentration of the test compound at which the ileum contraction reaction induced by leukotriene $D_4$ was inhibited by 50% (hereinafter referred to as $IC_{50}$). Specifically, at varying concentrations of each test compound, the percent inhibition of contraction was calculated from the measured degree of contraction of the ileum according to the following equation:

Percent inhibition of contraction =

$$\frac{\text{(Degree of contraction without addition of test compound)} - \text{(Degree of contraction with addition of test compound)}}{\text{(Degree of contraction without addition of test compound)}} \times 100$$

On the basis of the data thus obtained, a dose-response curve was prepared and used to determine the $IC_{50}$ value of the test compound.

The results thus obtained are shown in Table 1. For purposes of comparison, the antagonistic effect on leukotriene $D_4$ of Compound TBX was tested in the same manner as described above and the result is also shown in Table 1. Among the test compounds indicated, the compounds of Examples 1, 6 and 9 were prepared according to procedure a described in the respective examples.

TABLE 1

| Test compound | Antagonistic effect on leukotriene $D_4$ $IC_{50}$ (μg/ml) |
| --- | --- |
| Compound TBX | 200 |
| Example 1 | 0.03 |
| Example 2 | 0.10 |
| Example 3 | 0.20 |
| Example 4 | 1.00 |
| Example 5 | 0.80 |
| Example 6 | 0.01 |
| Example 7 | 0.10 |
| Example 8 | 0.70 |
| Example 9 | 0.005 |
| Example 10 | 0.60 |
| Example 11 | 0.90 |
| Example 12 | 0.03 |
| Example 13 | 0.005 |

As is evident from Table 1, it may be recognized that the present compounds [I] and physiologically acceptable salts thereof exhibit a marked antagonistic effect on leukotriene $D_4$ which cannot be predicted from Compound TBX.

(ii) In vivo tests

Using male guinea pigs of the Hartley strain, weighing about 400 g, in groups of six, the inhibitory effect of the present compounds [I] and physiologically acceptable salts thereof on a Type I allergic reaction induced by leukotriene $D_4$ was tested in two dosage forms (i.e., by intravenous injection and by oral administration) according to the Konzett-Rössler procedure [Naunyn-Schmiederbergs Archiv für Experimentelle Pathologie und Pharmakologie, Vol. 195, p. 71, 1940]. Specifically, each guinea pig was anesthetized by intraperitoneal administration of 1.5 g/kg of urethane and an incision was made in the neck to expose the trachea. To the exposed trachea was connected a respirator (with a ventilation volume of 5-7 ml, a respiration rate of 70 per minute, and a pulmonary load pressure of 10 cmH$_2$O; manufactured by Ugo Basile Biological Research Apparatus Co.) by way of a cannula. The volume of air overflowing through the branch of the cannula was measured by means of a Model 7020 Bronchospasm Transducer (manufactured by Ugo Basile Biological Research Apparatus Co.) and recorded with a Model RM-6000 Polygraph (manufactured by Nippon Koden Co., Ltd.).

Intravenous injection tests were carried out as follows: Each guinea pig was treated by intravenous injection of 1 mg/kg of gallamine triethiodide. Then, 20.0 to 6000.0 μg/kg of a test compound and 0.5 μg/kg of leukotriene $D_4$ were successively administered thereto through the cervical vein with an interval of 2 minutes. The volume of air overflowing as a result of the induced airway constriction reaction was measured. The test compound was used in the form of a solution in physiological saline containing sodium hydrogen carbonate or potassium carbonate.

Oral administration tests were carried out as follows: 1 to 30 mg/kg of a test compound was orally administered to each guinea pig 90 minutes before anesthesia with urethane. Then, the anesthetized guinea pig was treated by intravenous injection of 1 mg/kg of gallamine triethiodide and administration of 0.5 μg/kg of leukotriene $D_4$ through the cervical vein. The volume of air overflowing as a result of the induced airway constriction reaction was measured.

Both in the intravenous injection tests and in the oral administration tests, leukotriene $D_4$ was used in the form of a solution in physiological saline.

Both in the intravenous injection tests and in the oral administration tests, the pharmacological effect on the Type I allergic reaction was evaluated in terms of the dose of the test compound at which the airway constriction reaction induced by leukotriene $D_4$ was inhibited by 50% (hereinafter referred to as $ID_{50}$), provided that $ID_{50}$ was expressed in μg/kg for the intravenous injection tests and in mg/kg for the oral administration tests. Specifically, at 4 to 6 different doses of each test compound ranging from 20.0 to 6000.0 μg/kg for the intravenous injection tests and from 1 to 30 mg/kg for the oral administration tests, the percent inhibition of the airway constriction reaction was calculated according to the following equation:

$$\text{Percent inhibition} = \frac{X - Y}{X} \times 100$$

where X is the ratio of the incremental volume of overflowing air measured in the leukotriene $D_4$-treated group to the incremental volume of overflowing air measured when the airway of the guinea pig is perfectly constricted, and Y is the ratio of the incremental volume of overflowing air measured in the test compound- and leukotriene $D_4$-treated group to the incremental volume of overflowing air measured when the airway of the guinea pig is perfectly constricted. On the basis of the data thus obtained, a dose-response curve was prepared and used to determine the $ID_{50}$ value of the test compound.

The results thus obtained are shown in Table 2. For purposes of comparison, the $ID_{50}$ value of Compound TBX was determined in the same manner as described above in connection with the intravenous injection tests, except that its doses ranged from 5 to 10 mg/kg, and the result is also shown in Table 2. Among the test compounds indicated, the compounds of Examples 1, 6 and 9 used in the intravenous injection tests were prepared according to procedure a described in the respective examples, and those used in the oral administration tests were prepared according to procedure b.

TABLE 2

| Test compound | Inhibitory effect on Type I allergic reaction | |
|---|---|---|
| | $ID_{50}$ (intravenous; μg/kg) | $ID_{50}$ (oral; mg/kg) |
| Compound TBX | 10000 or greater | |
| Example 1 | 97 | 9 |
| Example 2 | 160 | |
| Example 3 | 170 | |
| Example 4 | 4900 | |
| Example 6 | 110 | 10 |
| Example 8 | 1900 | |
| Example 9 | 38 | 5 |
| Example 11 | 2900 | |
| Example 12 | 97 | 10 |

As is evident from Table 2, it may be recognized that the present compounds [I] and physiologically acceptable salts thereof can antagonistically and markedly inhibit leukotriene $D_4$-induced Type I allergic reactions as represented by the airway constriction reaction.

(iii) Toxicity test

The acute toxicity ($LD_{50}$) of several typical examples of the present compounds [I] and physiologically acceptable salts thereof was tested on 5-weeks-old male ddY strain mice and male SD strain rats. For this purpose, the compounds of Examples 1, 6 and 9 were selected as typical examples. For mice, the $LD_{50}$ values of these three compounds were not less than 4.0 g/kg when administered orally, and not less than 100 mg/kg when administered intravenously. For rats, their $LD_{50}$ values were not less than 4.0 g/kg when administered orally, and not less than 200 mg/kg when administered intravenously.

As can be seen from the results of the above-described in vitro tests, in vivo tests and toxicity tests, the present compounds [I] and physiologically acceptable salts thereof are useful for the treatment of SRS-A induced Type I allergic diseases including, in particular, bronchial asthma and allergic rhinitis. They can also be used as anti-ulcer agents, anti-inflammatory agents or drugs for the treatment of ischemic heart diseases.

The present compounds [I] and physiologically acceptable salts thereof may be admixed with physiologically inert solid or liquid pharmaceutical carriers to form pharmaceutical compositions. These compositions may have a variety of dosage forms including injectable solutions, tablets, capsules, powders, fine granules, granules, liquors, suspensions and emulsions. The pharmaceutical carriers can be any of various pharmaceutical carriers usually used in such dosage forms, and examples thereof include excipients, binders and disintegrants, such as corn starch, dextrin, α-, β- or γ-cyclodextrin, glucose, lactose, sucrose, methylcellulose, calcium carboxymethylcellulose, crystalline cellulose, magnesium stearate, sodium alginate, Witepsol W35, Witepsol E85, polyvinyl alcohol, light silicic acid anhydride, etc.; lubricants such as talc, stearic acid, waxes, hydroxypropylcellulose, boric acid, etc.; coating agents such as shellac, cellulose acetate phthalate, polyvinyl acetal diethylaminoacetate, etc.; solubilizing agents such as glycerol, propylene glycol, mannitol, etc.; emulsifying or suspending agents such as polyoxyethylene stearate, polyoxyethylene cetyl alcohol ether, gum arabic, polyvinylpyrrolidone, etc.; stabilizers such as sorbitol, Tween 80, Span 60, fats and oils, etc.; and various solvents.

In the above-described pharmaceutical compositions, the present compound [I] or a pharmaceutically acceptable salt thereof should be contained in such an amount that the daily dose of the active ingredient is in the range of 0.002 to 60 mg/kg, preferably 0.02 to 10 mg/kg, for purposes of oral administration or in the range of 1 to 1000 μg/kg, preferably 10 to 200 μg/kg, for purposes of intravenous injection.

The present invention is further illustrated by the following Reference Examples, Examples and Pharmaceutical Compositions.

REFERENCE EXAMPLES 1.30 g (4.92 mmoles) of 9-bromomeothyl-3-cyano-4H-pyrido[1,2-a]pyrimidin-4-one, 0.97 g (5.00 mmoles) of 2,4-dihydroxy-3-n-propylacetophenone and 0.60 g of anhydrous potassium carbonate were added to 100 ml of methyl ethyl ketone, and this mixture was heated under reflux for 45 minutes. After cooling, the crystals which separated out of the reaction solution were collected by filtration and washed with water to obtain 1.10 g (59% yield) of 9-[(4-acetyl-3-hydroxy-2-n-propylphenoxy)methyl]-3-cyano-4H-pyrido[1,2-a]pyrimidin-4-one. These crystals had a melting point of 233°-234° C.

The following 18 nitrile derivatives [II] were prepared in substantially the same manner as described above, except that the 9-bromomethyl-3-cyano-4H-pyrido[1,2-a]pyrimidin-4-one was replaced by each of the corresponding compounds [III] and the reaction conditions (such as the molar ratio of reactants, reaction solvent, reaction temperature, reaction time, etc.) were suitably modified. Thus, these nitrile derivatives [II] were obtained in a yield ranging from 50% to 85%.

7-[(4-Acetyl-3-hydroxy-2-n-propylphenoxy)methyl]-3-cyano-4H-pyrido[1,2-a]pyrimidin-4-one.

8-[(4-Acetyl-3-hydroxy-2-n-propylphenoxy)methyl]-3-cyano-4H-pyrido[1,2-a]pyrimidin-4-one.

9-[(4-Acetyl-3-hydroxy-2-n-propylphenoxy)methyl]-7-bromo-3-cyano-4H-pyrido[1,2-a]pyrimidin-4-one.

9-[(4-Acetyl-3-hydroxy-2-n-propylphenoxy)methyl]-3-cyano-7-methyl-4H-pyrido[1,2-a]pyrimidin-4-one.

9-[(4-Acetyl-3-hydroxy-2-n-propylphenoxy)methyl]-3-cyanomethyl-4H-pyrido[1,2-a]pyrimidin-4-one.

7-[(4-Acetyl-3-hydroxy-2-n-propylphenoxy)methyl]-3-cyanomethyl-4H-pyrido[1,2-a]pyrimidin-4-one.

9-[(4-Acetyl-3-hydroxy-2-n-propylphenoxy)methyl]-3-cyanomethyl-7-methyl-4H-pyrido[1,2-a]pyrimidin-4-one.

9-[(4-Acetyl-3-hydroxy-2-n-propylphenoxy)methyl]-3-(2-cyanoethyl)-4H-pyrido[1,2-a]pyrimidin-4-one.

8-[(4-Acetyl-3-hydroxy-2-n-propylphenoxy)methyl]-3-(2-cyanoethyl)-4H-pyrido[1,2-a]pyrimidin-4-one.

9-[(4-Acetyl-3-hydroxy-2-n-propylphenoxy)methyl]-7-bromo-3-(2-cyanoethyl)-4H-pyrido[1,2-a]pyrimidin-4-one.

9-[(4-Acetyl-3-hydroxy-2-n-propylphenoxy)methyl]-8-chloro-3-cyano-4H-pyrido[1,2-a]pyrimidin-4-one.

9-[(4-Acetyl-3-hydroxy-2-n-propylphenoxy)methyl]-3-cyano-6-fluoro-4H-pyrido[1,2-a]pyrimidin-4-one.

7-[(4-Acetyl-3-hydroxy-2-n-propylphenoxy)methyl]-8-chloro-3-cyano-4H-pyrido[1,2-a]pyrimidin-4-one.

9-[(4-Acetyl-3-hydroxy-2-n-propylphenoxy)methyl]-3-cyano-8-methyl-4H-pyrido[1,2-a]pyrimidin-4-one.

7-[(4-Acetyl-3-hydroxy-2-n-propylphenoxy)methyl]-8-bromo-3-cyanomethyl-4H-pyrido[1,2-a]pyrimidin-4-one.

8-[(4-Acetyl-3-hydroxy-2-n-propylphenoxy)methyl]-9-chloro-3-cyanomethyl-4H-pyrido[1,2-a]pyrimidin-4-one.

9-[(4-Acetyl-3-hydroxy-2-n-propylphenoxy)methyl]-3-(2-cyanoethyl)-6-fluoro-4H-pyrido[1,2-a]pyrimidin-4-one.

7-[(4-Acetyl-3-hydroxy-2-n-propylphenoxy)methyl]-3-(2- -cyanoethyl)-8-methyl-4H-pyrido[1,2-a]pyrimidin-4-one.

EXAMPLE 1

(Procedure a)

A mixture of 1.00 g (2.65 mmoles) of 9-[(4-acetyl-3-hydroxy-2-n-propylphenoxy)methyl]-3-cyano-4H-pyrido[1,2-a]pyrimidin-4-one, 0.97 g (7.27 mmoles) of aluminum chloride, 1.43 g (21.99 mmoles) of sodium azide and 20 ml of tetrahydrofuran was heated under reflux for 2 hours. After cooling, the resulting reaction solution was diluted with ice water and then acidified with dilute hydrochloric acid. The precipitate so formed was collected by filtration and recrystallized from dimethyformamide to obtain 0.72 g (65% yield) of 9-[(4-acetyl-3-hydroxy-2-n-propylphenoxy)methyl]-3-(1H-tetrazol-5-yl)-4H-pyrido[1,2-a]-pyrimidin-4-one in the form of white crystals. These crystals had a melting point of 269°-271° C. (dec.).

Infrared absorption spectrum (KBr, cm$^{-1}$): 3240, 1680, 1625, 1270.

Analysis: Calcd. for $C_{21}H_{20}N_6O_4$ (%): C, 59.99; H, 4.80; N, 19.99. Found: (%): C, 60.12; H, 4.71; N, 19.73.

(Procedure b)

A mixture of 1.00 g (2.65 mmoles) of 9-[(4-acetyl-3-hydroxy-2-n-propylphenoxy)methyl]-3-cyano-4H-pyrido[1,2-a]-pyrimidin-4-one, 0.97 g (7.27 mmoles) of aluminum chloride, 1.43 g (21.99 mmoles) of sodium azide and 20 ml of tetrahydrofuran was heated under reflux for 2 hours. After cooling, the resulting reaction solution was diluted with ice water and then acidified with dilute hydrochloric acid. The precipitate so formed was collected by filtration and dried. 1.09 g (2.59 mmoles) of this precipitate was suspended in 55 ml of menthanol and then dissolved therein by adding 3.00 ml (2.55 mmoles) of a 5.6% ethanolic solution of potassium hydroxide. The resulting solution was filtered to remove any insoluble matter, and the filtrate was cooled. The precipitate which separated out was collected by filtration to obtain 0.88 g (74% yield) of 9-[(4-acetyl-3-hydroxy-2-n-propylphenoxy)methyl]-3-(1H-tetrazol-5-yl)-4H-pyrido[1,2-a]pyrimidin-4-one potassium salt. Subsequently, 0.88 g (1.92 mmoles) of this potassium salt was dissolved in 180 ml of water by warming and the resulting solution was neutralized with 1.23 ml (3.69 mmoles) of 3N hydrochloric acid. The precipitate so formed was collected by filtration to obtain 0.78 g (97% yield) of 9-[(4-acetyl-3- hydroxy-2-n-propylphenoxy)methyl]-3-(1H-tetrazol-5-yl)-4H-pyrido[1,2-a]pyrimidin-4-one in the form of a white powder. This powder had a melting point of 268°-271° C. (dec.) and its infrared absorption spectrum and elemental analysis were as follows:

Infrared absorption spectrum (KBr, cm$^{-1}$): 3240, 1680, 1625, 1270.

Analysis: Calcd. for $C_{21}H_{20}N_6O_4$ (%): C, 59.99; H, 4.80; N, 19.99. Found (%): C, 59.95; H, 4.73; N, 20.06.

The compounds of the following Examples 2-5 were prepared by repeating the above-described procedure a of Example 1 except that the 9-[(4-acetyl-3-hydroxy-2-n-propylphenoxy)methyl]-3-cyano-4H-pyrido[1,2-a]pyrimidin-4-one (2.65 mmoles) was replaced by each of the corresponding nitrile derivatives [II] (2.65 mmoles).

EXAMPLE 2

There was obtained 0.19 g (17% yield) of 7-[(4-acetyl-3-hydroxy-2-n-propylphenoxy)methyl]-3-(1H-tetrazol-5-yl)-4H-pyrido[1,2-a]pyrimidin-4-one in the form of white crystals. These crystals, which were recrystallized from acetonitrile, had a melting point of 256°–260° C. (dec.).

Infrared absorption spectrum (KBr, cm$^{-1}$): 3240, 1675, 1640, 1275.

Analysis: Calcd. for $C_{21}H_{20}N_6O_4$ (%); C, 59.99; H, 4.80; N, 19.99 Found (%): C, 59.72; H, 4.94; N, 19.83.

EXAMPLE 3

There was obtained 0.26 g (23% yield) of 8-[(4-acetyl-3-hydroxy-2-n-propylphenoxy)methyl]-3-(1H-tetrazol-5-yl)-4H-pyrido[1,2-a]pyrimidin-4-one in the form of white crystals. These crystals, which were recrystallized from dimethylformamide, had a melting point of 263°–272° C. (dec.).

Infrared absorption spectrum (KBr, cm$^{-1}$): 3230, 1670, 1635, 1280.

Analysis: Calcd. for $C_{21}H_{20}N_6O_4$ (%) C, 59.99; H, 4.80; N, 19.99. Found (%): C, 59.83; H, 4.79; N, 19.86.

EXAMPLE 4

There was obtained 0.12 g (9% yield) of 9-[(4-acetyl-3-hydroxy-2-n-propylphenoxy)methyl]-7-bromo-3-(1H-tetrazol-5-yl)-4H-pyrido[1,2-a]pyrimidin-4-one in the form of pale-yellow crystals. These crystals, which were recrystallized from a mixture of tetrahydrofuran and methanol, had a melting point of 240° C. (dec.).

Infrared absorption spectrum (KBr, cm$^{-1}$): 3235, 1700, 1620, 1275.

Analysis: Calcd. for $C_{21}H_{19}BrN_6O_4$ (%): C, 50.51; H, 3.84; N, 16.83. Found (%): C, 50.56; H, 3.90; N, 16.74.

EXAMPLE 5

There was obtained 0.59 g (51% yield) of 9-[(4-acetyl-3-hydroxy-2-n-propylphenoxy)methyl]-7-methyl-3-(1H-tetrazol-5-yl)-4H-pyrido[1,2-a]pyrimidin-4-one in the form of white crystals. These crystals, which were recrystallized from dimethylformamide, had a melting point of 279°–280° C. (dec.).

Infrared absorption spectrum (KBr, cm$^{-1}$): 3230, 1670, 1630, 1275.

Analysis: Calcd. for $C_{22}H_{22}N_6O_4$ (%): C, 60.82; H, 5.10; N, 19.35. Found (%): C, 60.98; H, 5.03; N, 19.20.

EXAMPLE 6

(Procedure a)

A mixture of 1.04 g (2.65 mmoles) of 9-[(4-acetyl-3-hydroxy-2-n-propylphenoxy)methyl]-3-cyanomethyl-4H-pyrido[1,2-a]pyrimidin-4-one, 1.00 g (18.69 mmoles) of ammonium chloride, 1.21 g (18.61 mmoles) of sodium azide and 30 ml of dimethylformamide was heated at 100°–110° C. for 8 hours with stirring. After cooling, the resulting reaction solution was poured into ice water and then acidified with dilute hydrochloric acid. The precipitate so formed was collected by filtration and recrystallized from dimethylformamide to obtain 0.55 g (48% yield) of 9-[(4-acetyl-3-hydroxy-2-n-propylphenoxy)methyl]-3-[(1H-tetrazol-5-yl)methyl]-4H-pyrido[1,2-a]pyrimidin-4-one in the form of pale-yellow crystals. These crystals had a melting point of 250°–253° C. (dec.).

Infrared absorption spectrum (KBr, cm$^{-1}$): 1680, 1630, 1265.

Analysis: Calcd. for $C_{22}H_{22}N_6O_4$ (%): C, 60.82; H, 5.10; N, 19.35. Found (%): C, 61.05; H, 5.08; N, 19.42.

(Procedure b)

A mixture of 1.04 g (2.65 mmoles) of 9-[(4-acetyl-3-hydroxy-2-n-propylphenoxy)methyl]-3-cyanomethyl-4H-pyrido[1,2-a]pyrimidin-4-one, 1.00 g (18.69 mmoles) of ammonium chloride, 1.21 g (18.61 mmoles) of sodium azide and 30 ml of dimethylformamide was heated at 100°–110° C. for 8 hours with stirring. After cooling, the resulting reaction solution was poured into ice water and then acidified with dilute hydrochloric acid. The precipitate so formed was collected by filtration and then dried. 1.10 g (2.53 mmoles) of this precipitate was suspended in 70 ml of methanol and dissolved therein by adding 2.30 ml (2.30 mmoles) of a 4.2% aqueous solution of sodium hydroxide. The resulting solution was filtered to remove any insoluble matter. The filtrate was evaporated to dryness under reduced pressure to obtain 1.05 g (91% yield) of 9-[(4-acetyl-3-hydroxy-2-n-propylphenoxy)methyl]-3-[(1H-tetrazol-5-yl)methyl]-4H-pyrido[1,2-a]pyrimidin-4-one sodium salt. Subsequently, 1.05 g (2.30 mmoles) of this sodium salt was dissolved in 260 ml of water and the resulting solution was neutralized with 1.50 ml (4.50 mmoles) of 3N hydrochloric acid. The precipitate so formed was collected by filtration and then dried to obtain 0.97 g (97% yield) of 9-[(4-acetyl-3-hydroxy-2-n-propylphenoxy)methyl]-3-[(1H-tetrazol-5-yl)methyl]-4H-pyrido[1,2-a]pyrimidin-4-one in the form of a pale-yellow powder. This powder had a melting point of 248°–253° C. (dec.) and its infrared absorption spectrum and elemental analysis were as follows:

Infrared absorption spectrum (KBr, cm$^{-1}$): 1680, 1630, 1265.

Analysis: Calcd. for $C_{22}H_{22}N_6O_4$ (%): C, 60.82; H, 5.10; N, 19.35. Found (%): C, 60.56; H, 5.32; N, 19.20.

The compounds of the following Examples 7 and 8 were prepared by repeating the above-described procedure a of Example 6 except that the 9-[(4-acetyl-3-hydroxy-2-n-propylphenoxy)methyl]-3-cyanomethyl-4H-pyrido[1,2-a]pyrimidin-4-one (2.65 mmoles) was replaced by each of the corresponding nitrile derivatives [II] (2.65 mmoles).

EXAMPLE 7

There was obtained 0.44 g (38% yield) of 7-[(4-acetyl-3-hydroxy-2-n-propylphenoxy)methyl]-3-[(1H-tetrazol-5-yl)methyl]-4H-pyrido[1,2-a]pyrimidin-4-one in the form of pale-yellow crystals. These crystals, which were recrystallized from acetic acid, had a melting point of 228°–232° C. (dec.).

Infrared absorption spectrum (KBr, cm $^{-1}$): 1675, 1635, 1275.

Analysis: Calcd. for $C_{22}H_{22}N_6O_4$ (%): C, 60.82; H, 5.10; N, 19.35. Found (%): C, 60.80; H, 5.18; N, 19.30.

EXAMPLE 8

There was obtained 0.62 g (52% yield) of 9-[(4-acetyl-3-hydroxy-2-n-propylphenoxy)methyl]-7-methyl-3-[(1H-tetrazol-5-yl)methyl]-4H-pyrido[1,2-a]pyrimidin-4-one in the form of white crystals. These crystals, which were recrystallized from dimethylformamide, had a melting point of 234°–238° C. (dec.).

Infrared absorption spectrum (KBr, cm$^{-1}$): 1670, 1625, 1265.

Analysis: Calcd. for $C_{23}H_{24}N_6O_4$ (%): C, 61.59; H, 5.39; N, 18.74. Found (%): C, 61.76; H, 5.31; N, 18.96.

EXAMPLE 9

(Procedure a)

A mixture of 1.07 g (2.65 mmoles) of 9-[(4-acetyl-3-hydroxy-2-n-propylphenoxy)methyl ]-3-(2-cyanoethyl)-4H-pyrido[1,2-a]pyrimidin-4-one, 1.76 g 2.57 g (39.53 mmoles) of sodium azide and 45 ml of tetrahydrofuran was heated under reflux for 23 hours. After cooling, the resulting reaction solution was poured into ice water and then acidified with dilute hydrochloric acid. The precipitate so formed was separated by filtration and recrystallized from acetonitrile to obtain 0.70 g (59% yield) of 9-[(4-acetyl-3-hydroxy-2-n-propylphenoxy)methyl]-3-[2-(1H-tetrazol-5-yl)ethyl]-4H-pyrido[1,2-a]pyrimidin-4-one in the form of white crystals. These crystals had a melting point of 238°–239° C. (dec.).

Infrared absorption spectrum (KBr, cm×1): 1670, 1620, 1270.

Analysis: Calcd. for $C_{23}H_{24}N_6O_4$ (%): C, 61.59; H, 5.39; N, 18.74. Found (%)! C, 61.64; H, 5.30; N, 18.76.

(Procedure b)

A mixture of 1.07 g (2.65 mmoles)of 9-[(4-acetyl-3-hydroxy-2-n-propylphenoxy)methyl]-3-(2-cyanoethyl)-4H-pyrido[1,2-a]pyrimidin-4-one, 1.76 g (13.20 mmoles) of aluminum chloride, 2.57 g (39.53 mmoles) of sodium azide and 45 ml of tetrahydrofuran was heated under reflux for 23 hours. After cooling, the resulting reaction solution was poured into ice water and then acidified with dilute hydrochloric acid. The precipitate so formed was separated by filtration and then dried. 1.14 g (2.54 mmoles) of this precipitate was suspended in 250 ml of water and dissolved therein by adding 2.69 ml (2.29 mmoles) of a 5.6% aqueous solution of potassium hydroxide. After the resulting solution was filtered to remove any insoluble matter, the filtrate was freeze-dried to obtain 1.11 g (90% yield) of 9-[(4-acetyl-3-hydroxy-2-npropylphenoxy)methyl]-3-[2-(1H-tetrazol-5-yl)ethyl]-4H-pyrido[1,2-a]pyrimidin-4-one potassium salt. Subsequently, 1.11 g (2.28 mmoles) of this potassium salt was dissolved in 250 ml of water and the resulting solution was neutralized with 1.50 ml (4.50 mmoles) of 3N hydrochloric acid. The precipitate so formed was collected by filtration and then dried to obtain 1.00g (98% yield) of 9-[(4-acetyl-3-hydroxy-2-n-propylphenoxy)methyl]-3-[2-(1H-tetrazol-5-yl)ethyl]-4H-pyrido[1,2-a]pyrimidin-4-one in the form of a white powder. This powder had a melting point of 236°–239° C. (dec.) and its infrared absorption spectrum and elemental analysis were as follows:

Infrared absorption spectrum (KBr, cm$^{-1}$): 1670, 1620, 1270.

Analysis: Calcd. for $C_{23}H_{24}N_6O_4$ (%): C, 61.59; H, 5.39; N, 18.74. Found (%): C, 61.32; H, 5.51; N, 18.63.

The compounds of the following Examples 10 and 11 were prepared by repeating the above-described procedure a of Example 9 except that the 9-[(4-acetyl-3-hydroxy-2-n-propylphenoxy)methyl]-3-(2-cyanoethyl)-4H-pyrido[1,2-a]pyrimidin-4-one (2.65 mmoles) was replaced by each of the corresponding nitrile derivatives [II] (2.65 mmoles).

EXAMPLE 10

There was obtained 0.43 g (36% yield) of 8-[(4-acetyl-3-hydroxy-2-n-propylphenoxy)methyl]-3-[2-(1H-tetrazol-5-yl)ethyl]-4H-pyrido[1,2-a]pyrimidin-4-one in the form of white crystals. These crystals, which were recrystallized from dimethylformamide, had a melting point of 226°–230° C. (dec.).

Infrared absorption spectrum (KBr, cm$^{-1}$): 1675, 1620, 1265.

Analysis: Calcd. for $C_{23}H_{24}N_6O_4$ (%): C, 61.59; H, 5.39; N, 18.74. Found (%): C, 61.32; H, 5.48; N, 18.63.

EXAMPLE 11

There was obtained 0.25 g (18% yield) of 9-[(4-acetyl-3-hydroxy-2-n-propylphenoxy)methyl]-7-bromo-3-[2-(1H-tetrazol-5yl)ethyl]-4H-pyrido[1,2-a]pyrimidin-4-one in the form of pale-yellow crystals. These crystals, which were recrystallized from acetonitrile, had a melting point of 220°–223° C. (dec.).

Infrared absorption spectrum (KBr, cm.$^{-1}$): 1680, 1630, 1275.

Analysis: Calcd. for $C_{23}H_{23}BrN_6O_4$ (%): C, 52.38; H, 4.40; N, 15.94. Found (%) : C, 52.43; H, 4.38; N, 16.04.

EXAMPLE 12

1.00 g (2.38 mmoles) of 9-[(4-acetyl-3-hydroxy-2-n-propylphenoxy)methyl]-3-(1H-tetrazol-5-yl)-4H-pyrido[1,2-a]pyrimidin-4-one was suspended in 50 ml of methanol and dissolved therein by adding 2.75 ml (2.34 mmoles) of a 5.6% ethanolic solution of potassium hydroxide. The resulting solution was filtered to remove any insoluble matter, and the filtrate was cooled. The precipitate which separated out was collected by filtration to obtain 0.81 g (74% yield) of 9-[(4-acetyl-3-hydroxy-2-n-propylphenoxy)methyl]-3-(1H-tetrazol-5-yl)-4H-pyrido[1,2-a]pyrimidin-4-one potassium salt in the form of a pale-yellow powder.

Infrared absorption spectrum (KBr, cm$_{-1}$): 1675, 1625, 1275.

Analysis: Calcd. for $C_{21}H_{19}KN_6O_4$ (%): C, 55.00; H, 4.18; N, 18.33. Found (%): C, 54.89; H, 4.23; N, 18.17.

EXAMPLE 13

1.00 g (2.23 mmoles) of 9-[(4-acetyl-3-hydroxy-2-n-propylphenoxy)methyl]-3-[2-(1H-tetrazol-5-yl)ethyl]-4H-pyrido-1,2-a]pyrimidin-4-one was suspended in 200 ml of water and dissolved therein by adding 2.62 ml (2.23 mmoles) of a 5.6% aqueous solution of potassium hydroxide. The resulting solution was filtered to remove any insoluble matter, and the filtrate was freeze-dried to obtain 1.06 g (98% yield) of 9-[(4-acetyl-3-hydroxy-2-n-propylphenoxy)methyl]-3-[2-(1H-tetrazol-5-yl)ethyl]-4H-pyrido[1,2-a]pyrimidin-4-one potassium salt in the form of a pale-yellow powder.

Infrared absorption spectrum (KBr, cm$^{-1}$): 1670, 1620, 1275.

Analysis: Calcd. for $C_{23}H_{23}N_6O_4$ (%): C, 56.77; H, 4.76; N, 17.28. Found (%): C, 56.61; H, 4.63; N, 17.16.

In addition, the nine compounds enumerated below were prepared in substantially the same manner as described above in Examples 1, 6, 9 and 13.

9-[(4-Acetyl-3-hydroxy-2-n-propylphenoxy)methyl]-8-chloro-3-(1H-tetrazol-5-yl)-4H-pyrido[1,2-a]pyrimidin-4-one.

9-[(4-Acetyl-3-hydroxy-2-n-propylphenoxy)methyl]-6-fluoro-3-(1H-tetrazol-5-yl)-4H-pyrido[1,2-a]pyrimidin-4-one.

7-[(4-Acetyl-3-hydroxy-2-n-propylphenoxy)methyl]-8-chloro-3-(1H-tetrazol-5-yl)-4-pyrido[1,2-a]pyrimidin-4-one.

9-[(4-Acetyl-3-hydroxy-2-n-propylphenoxy)methyl]-8-methyl-3-(1H-tetrazol-5-yl)-4H-pyrido[1,2-a]pyrimidin-4-one.

7-[(4-Acetyl-3-hydroxy-2-n-propylphenoxy)methyl]-8-bromo-3-[(1H-tetrazol-5-yl)methyl]-4H-pyrido[1,2-a]pyrimidin-4-one.

8-[(4-Acetyl-3-hydroxy-2-n-propylphenoxy)methyl]-9-chloro-3-[(1H-tetrazol-5-yl)methyl]-4H-pyrido[1,2-a]pyrimidin-4-one.

9-[(4-Acetyl-3-hydroxy-2-n-propylphenoxy)methyl]-6-fluoro-3-[2-(1H-tetrazol-5-yl)ethyl ]-4H-pyrido[1,2-a]pyrimidin-4-one.

7-[(4-Acetyl-3-hydroxy-2-n-propylphenoxy)methyl]-8-methyl-3-[2-(1H-tetrazol-5-yl)ethyl]-4H-pyrido[1,2-a]pyrimidin-4-one.

9-[(4-Acetyl-3-hydroxy-2-n-propylphenoxy)methyl]-3-[(1H-tetrazol-5-yl)methyl]-4H-pyrido[1,2-a]pyrimidin-4-one sodium salt.

| Pharmaceutical Composition 1 (tablets) | % by weight |
|---|---|
| (1) Compound of Example 1 (procedure b) | 10.0 |
| (2) Lactose | 56.0 |
| (3) Corn starch | 15.0 |
| (4) Crystalline cellulose | 15.0 |
| (5) Hydroxypropylcellulose | 3.0 |
| (6) Magnesium stearate | 1.0 |
| | 100.0 |

The above ingredients (1)–(5) were blended together. After the addition of water, the resulting mixture was granulated and then dried. The granules so formed were adjusted to a predetermined size range, and the ingredient (6) was added thereto. The resulting mixture was compressed to form tablets each containing 10 mg of the active ingredient. Other tablets were also prepared in the same manner as described above, except that the compound of Example 1 used as the active ingredient was replaced by each of the compounds of Examples 6 and 9 (both prepared according to procedure b).

| Pharmaceutical Composition 2 (capsules) | % by weight |
|---|---|
| (1) Compound of Example 9 (procedure b) | 10.0 |
| (2) Lactose | 65.5 |
| (3) Corn starch | 20.0 |
| (4) Hydroxypropylcellulose | 3.0 |
| (5) Light silicic acid anhydride | 0.5 |
| (6) Magnesium stearate | 1.0 |
| | 100.0 |

According to conventional procedure, the above ingredients were blended together and then granulated. The granules so formed were filled into capsules, each of which contained 10 mg of the active ingredient. Other capsules were also prepared in the same manner as described above, except that the compound of Example 9 used as the active ingredient was replaced by each of the compounds of Examples 1 and 6 (both prepared according to procedure b).

What is claimed is:

1. A pyrido[1,2-a]pyrimidine compound of the formula

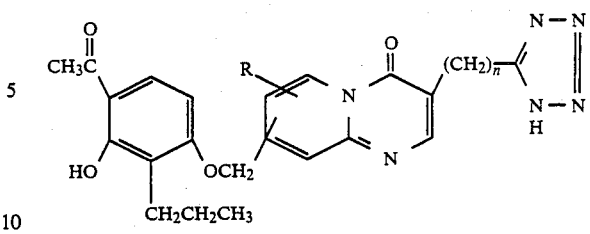

where R is a hydrogen atom, a halogen atom or a methyl group, and n is a whole number of 0, 1 or 2, or a physiologically acceptable salt thereof.

2. A compound as claimed in claim 1 which is
9-[(4-acetyl-3-hydroxy-2-n-propylphenoxy)methyl]-3-(1H-tetrazol-5-yl)-4H-pyrido[1,2-a]pyrimidin-4-one,
7-[(4-acetyl-3-hydroxy-2-n-propylphenoxy)methyl]-3-(1H-tetrazol-5-yl)-4H-pyrido[1,2-a]pyrimidin-4-one,
8-[(4-acetyl-3-hydroxy-2-n-propylphenoxy)methyl]-3-(1H-tetrazol-5-yl)-4H-pyrido[1,2-a]pyrimidin-4-one,
9-[(4-acetyl-3-hydroxy-2-n-propylphenoxy)methyl]-7-bromo-3(1H-tetrazol-5-yl)-4H-pyrido[1,2-a]pyrimidin-4-one,
9-[(4-acetyl-3-hydroxy-2-n-propylphenoxy)methyl]-7-methyl-3-(1H-tetrazol-5-yl)-4H-pyrido[1,2-a]pyrimidin-4-one,
9-[(4-acetyl-3-hydroxy-2-n-propylphenoxy)methyl]-3-[(1H-tetrazol-5-yl)methyl]-4H-pyrido[1,2-a]pyrimidin-4-one,
7-[(4-acetyl-3-hydroxy-2-n-propylphenoxy)methyl]-3-[(1H-tetrazol-5-yl)methyl]-4H-pyrido[1,2-a]pyrimidin-4-one,
9-[(4-acetyl-3-hydroxy-2-n-propylphenoxy)methyl]-7-methyl-3-[(1H-tetrazol-5-yl)methyl]-4H-pyrido[1,2-a]pyrimidin-4-one,
9-[(4-acetyl-3-hydroxy-2-n-propylphenoxy)methyl]-3-[2-(1H-tetrazol-5-yl)ethyl]-4H-pyrido[1,2-a]pyrimidin-4-one,
8-[(4-acetyl-3-hydroxy-2-n-propylphenoxy)methyl]-3-[2-(1H-tetrazol-5-yl)ethyl]-4H-pyrido[1,2-a]pyrimidin-4-one or
9-[(4-acetyl-3-hydroxy-2-n-propylphenoxy)methyl]-7-bromo-3-[2-(1H-tetrazol-5-yl)ethyl]-4H-pyrido[1,2-a]pyrimidin-4-one.

3. A compound as claimed in claim 1 wherein the physiologically acceptable salt is a potassium or sodium salt.

4. A compound as claimed in claim 3 which is 9-[(4-acetyl-3-hydroxy-2-n-propylphenoxy)methyl]3-(1H-tetrazol-5-yl)-4H-pyrido[1,2-a]pyrimidin-4-one potassium salt or 9-[(4-acetyl-3-hydroxy-2-n-propylphenoxy)methyl]3-[2-(1H-tetrazol-5-yl)ethyl-4H-pyrido-2-a]pyrimidin-4-one potassium salt.

5. Compound of claim 1 wherein R is a hydrogen atom.

6. Compound of claim 1 wherein n is 0.

7. Compound of claim 1 wherein n is 1.

8. Compound of claim 1 wherein n is 2.

9. Compound of claim 1 which is
9[((4-acetyl-3-hydroxy-2-n propylphenoxy)methyl-3-(1H-tetrazol-5-yl)-4H-pyrido[1,2a]pyrimidin-4-one.

10. Compound of claim 1 which is
9-[(4-acetyl-3-hydroxy-2-n-propylphenoxy)methyl-3-[(1H-tetrazol-5-yl)methyl]-4H-pyrido[1,2-a]pyrimidin-4-one.

11. Compound of claim 1 which is

9-[(4-acetyl-3-hydroxy-2-n-propylphenoxy)methyl-3-[2-(1H- tetrazol-5-yl)ethyl]-4H-pyrido[1,2-a]pyrimidin-4-one.

12. Compound of claim 1 which is 9-[(4-acetyl-3-hydroxy-2-n-prophenoxy)methyl-3-( 1H-tetrazol-5-yl)-4H-pyrido[1,2-a]pyrimidin-4-one potassium salt.

13. Compound of claim 1 which is 9-[(4-acetyl-3-hydroxy-2-n-propylphenoxyl)methyl-3-[(1H-tetrazol-5-yl) methyl]-4H-pyrido[1,2-a]pyrimidin-4-one sodium salt.

14. Compound of claim 1 which is 9-[(4-acetyl-3-hydroxy-2-n-propylphenoxy) methyl-3-[2-(1H-tetrazol-5-yl)ethyl]-4H-pyrido[,1,2-a]pyrimidin-4-one potassium salt.

15. A pharmaceutical composition useful for the treatment of allergic diseases containing, as an active ingredient, a pyrido[1,2-a]pyrimidine compound of the formula

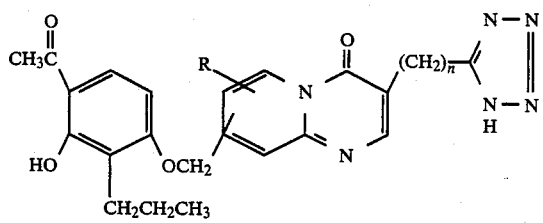

where R is a hydrogen atom, a halogen atom or a methyl group, and n is a whole number of 0, 1 or 2, or a physiologically acceptable salt thereof.

16. A pharmaceutical composition as claimed in claim 15 wherein the active ingredient is selected from the group consisting of 9-[(4-acetyl-3-hydroxy-2-n-propylphenoxy)methyl]3-(1H-tetraol-5-yl)-4H-pyrido[1,2-a]pyrimidin-4-one, 9-[(4-acetyl-3-hydroxy-2-n-propylphenoxy)methyl]-3-[( 1H-tetrazol-5-yl)methyl]-4H-pyrido[1,2-a]pyrimidin-4-one and 9-[(4-acetyl-3-hydroxy-2-n-propylphenoxy)methyl]-2-[2-(1H-tetrazol-5-yl)ethyl]-4H-pyrido[1,2-a]pyrimidin-4-one, as well as the potassium salts thereof.

17. Method of using a compound of claim 1 for treating allergic diseases induced by slow reacting substance of anaphylaxis comprising orally or intravenously administering a therapeutically effective amount of such compound of claim 1 to a patient.

18. Method of claim 17 wherein the allergic disease is bronchial asthma or allergic rhinitis.

19. Method of using a compound of claim 1 for treating allergic diseases induced by slow-reacting substance of anaphylaxis by direct antagonistic effect on the release of said substance of anaphylaxis in the living body for thereby directly inhibiting the activity in vivo of said substance of anaphylaxis after onset of an attack of such an allergic disease, comprising orally or intravenously administering a therapeutically effective amount of such compound of claim 1 to a patient.

20. Method of claim 19 wherein the allergic disease is bronchial asthma or allergic rhinitis.

21. Method of claim 19 wherein the compound is (1) 9-[(4-acetyl-3-hydroxy-2-n-propylphenoxy)methyl-3-(1H-tetrazol-5-yl)-4H-pyrido[1,2-a]pyrimidin-4-one, (2) 7-[(4-acetyl-3-hydroxy-2-n-propylphenoxy)methyl-3-(1H-tetrazol-5-yl)-4H-pyrido[1,2-a]pyrimidin-4-one, (3) 8-[(4-acetyl-3-hydroxy-2-n-propylphenoxy)methyl-3-(1H-tetrazol-5-yl)-4H-pyrido[1,2-a]pyrimidin-4-one, (4) 9-[(4-acetyl-3-hydroxy-2-n-propylphenoxy)methyl-7-bromo-3-(1H-tetrazol-5-yl)-4H-pyrido[1,2-a]pyrimidin-4-one, (5) 9-[(4-acetyl-3-hydroxy-2-n-propylphenoxy)methyl-7-methyl-3-(1H-tetrazol-5-yl)-4H-pyrido[1,2-a]pyrimidin-4-one, (6) 9-[(4-acetyl-3-hydroxy-2-n-propylphenoxy)methyl-3-[(1H-tetrazol-5-yl)methyl]-4H-pyrido[1,2-a]pyrimidin-4one, (7) 7-[(4-acetyl-3-hydroxy-2-n-propylphenoxy)methyl-3-[( 1H-tetrazol-5-yl)methyl]-4H-pyrido[1,2-a]pyrimidin-4-one, (8) 9-[(4-acetyl-3-hydroxy-2-n-propylphenoxy)methyl-7-methyl-3-[(1H-tetrazol-5-yl)methyl]-4H-pyrido[1,2-a]pyrimidin-4-one, (9) 9-[(4-acetyl-3-hydroxy-2-n-propylphenoxy)methyl-3-[2-(1H-tetrazol-5-yl)ethyl]-4H-pyrido[1,2-a]pyrimidin-4-one,

(10) 8-[(4-acetyl-3-hydroxy-2-n-propylphenoxy)methyl-3-[2-(1H-tetrazol-5-yl)ethyl]-4H-pyrido[1,2-a]pyrimidin-4-one, or

(11) 9-[(4-acetyl-3-hydroxy-2-n-propylphenoxy)methyl-7-bromo-3-[2-(1H-tetrzol-5-yl)ethyl]-4H-pyrido[1,2-a]pyrimidin-4-one.

22. Method of claim 19 wherein the compound is the physiologically acceptable potassium or sodium salt.

23. Method of claim 19 wherein R of the compound of the formula of claim 1 is a hydrogen atom.

24. Method of claim 19 wherein n of the compound of the formula of claim 1 is 0.

25. Method of claim 19 wherein n of the compound of the formula of claim 1 is 1.

26. Method of claim 19 wherein n of the compound of the formula of claim 1 is 2.

27. Method of claim 19 wherein the compound is 9-[(4-acetyl-3-hydroxy-2-n-propylphenoxy)methyl-3-(1H-tetrazol-5-yl)-4H-pyrido[1,2-a]pyrimidin-4-one.

28. Method of claim 19 wherein the compound is 9-[(4-acetyl-3-hydroxy-2-n-propylphenoxy)methyl-3-[( 1H-tetrazol-5-yl)methyl[-4H-pyrido[1,2-a]pyridin-4-one.

29. Method of claim 19 wherein the compound is 9-[(4-acetyl-3-hydroxy-2-n-propylphenoxy)methyl-3-[2-(1H-tetrazol-5-yl)ethyl]-4H-pyrido[1,2-a]pyrimidin-4-one.

30. Method of claim 19 wherein the compound is 9-[(4-acetyl-3-hydroxy-2-n-propylphenoxy)methyl-3-(1H-tetrazol5-yl)ethyl]-4H-pyrido[1,2-a]pyrimidin-4-one potassium salt.

31. Method of claim 19 wherein the compound is 9-[(4-acetyl-3-hydroxy-2-n-propylphenoxy)methyl-3-[(1H-tetrazol-5-yl)methyl]-4H-pyrido[1,2-a]pyrimidin-4-one sodium salt.

32. Method of claim 19 wherein the compound is 9-[(4-acetyl-3-hydroxy-2-n-propylphenoxy)methyl-3-[2-(1H-tetrazol-5-yl)ethyl]-4H-pyrido[1,2-a]pyrimidin-4-one potassium salt.

* * * * *